United States Patent [19]

Simms et al.

[11] 4,171,916

[45] Oct. 23, 1979

[54] APPARATUS AND METHOD FOR MEASURING THE CONSISTENCY OF A PULP SUSPENSION

[75] Inventors: Romilly J. Simms, Menlo Park; Byron K. Madsen, Saratoga, both of Calif.

[73] Assignee: Ishikawajima-Harima Heavy Industries Co., Ltd., Tokyo, Japan

[21] Appl. No.: 852,863

[22] Filed: Nov. 18, 1977

[51] Int. Cl.² ............................................. G01N 21/40
[52] U.S. Cl. .................................... 356/366; 162/263; 250/225; 356/442
[58] Field of Search ............... 356/115, 114, 116, 205, 356/206, 208, 117, 118, 119, 33–35, 90, 91, 92, 88, 364–370, 327, 434, 435, 436, 322; 250/225; 162/263

[56] References Cited

U.S. PATENT DOCUMENTS

| 3,283,644 | 11/1966 | Saltzman | 356/116 |
| 3,518,003 | 6/1970 | Meyn | 356/116 |
| 3,612,689 | 10/1971 | Liskowitz | 356/103 |

Primary Examiner—John K. Corbin
Assistant Examiner—B. Arnold
Attorney, Agent, or Firm—Lowhurst & Aine

[57] ABSTRACT

A consistency measuring apparatus and a method for determining fiber concentration of a pulp suspension, which utilizes a flow cell having a pair of parallel, light transparent side walls to allow the sample to be monitored to flow therethrough. A plane polarized beam of light is transmitted through the cell and received by a pair of detectors which have overlying plane polarized light analyzers, one having its axis of transmission crossed with and the other having its axis of transmission parallel to the plane of polarization of the transmitted light beam. The detectors provide electrical signals which are processed to give the consistency of the pulp suspension sample.

11 Claims, 4 Drawing Figures

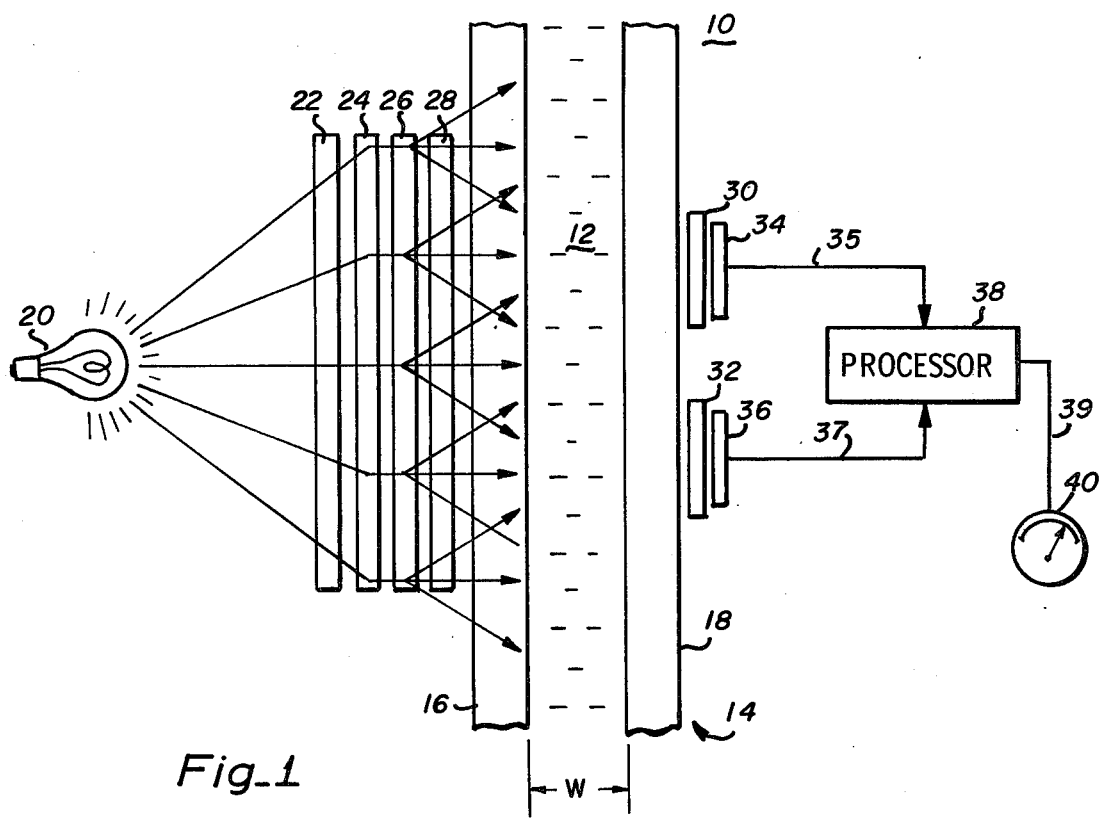
Fig_1
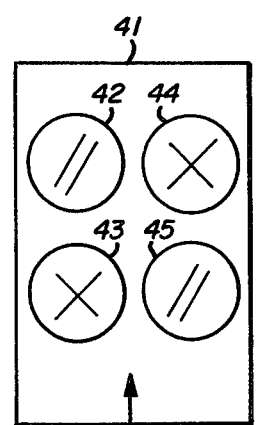
Fig_2
PULP FLOW

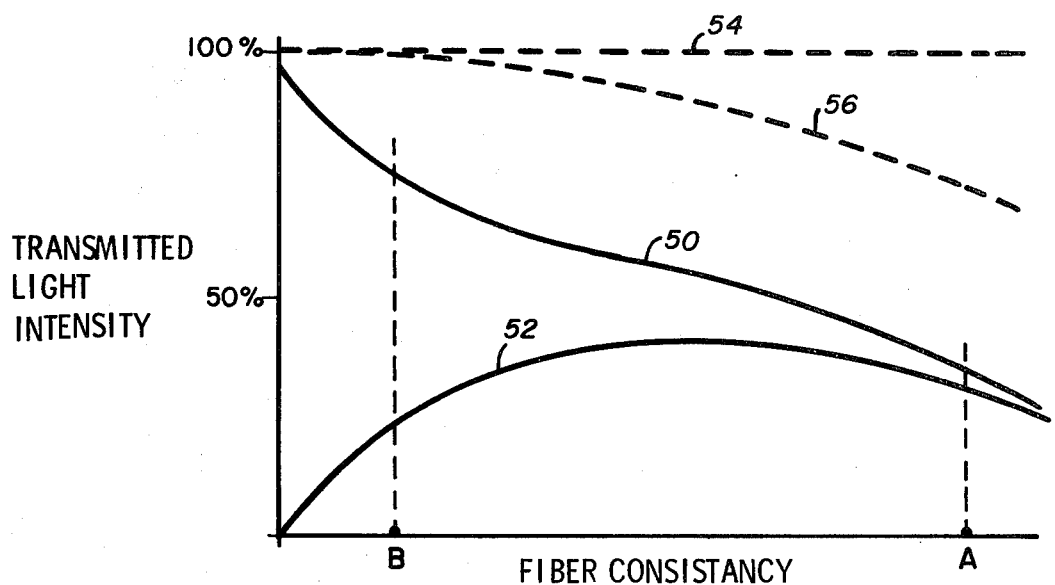
Fig_3
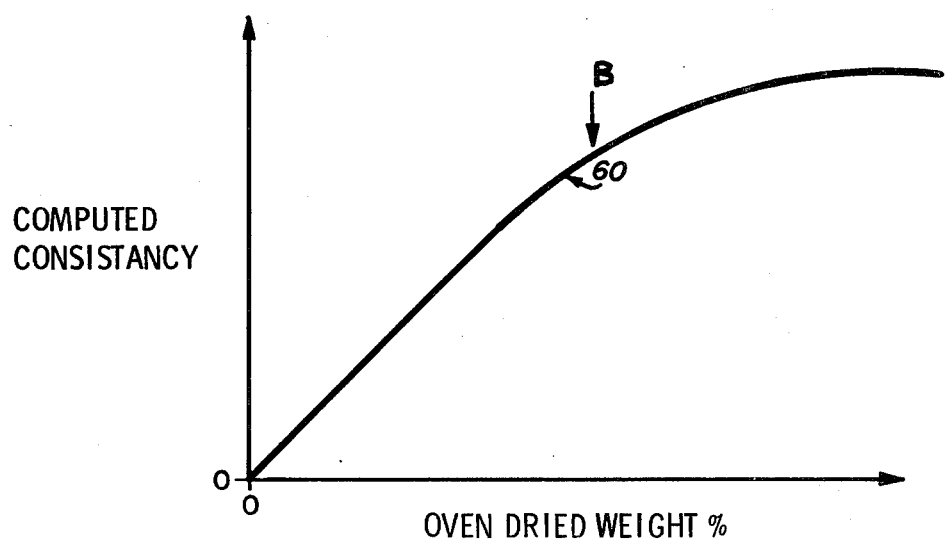
Fig_4

APPARATUS AND METHOD FOR MEASURING THE CONSISTENCY OF A PULP SUSPENSION

BACKGROUND OF THE INVENTION

This invention relates to an apparatus and a method for determining the mass concentration of cellulose fibers in a water suspension and more particularly to an on-line apparatus and a method for measuring and monitoring the consistency of a flowing pulp suspension.

The pulp and paper industry has several requirements to measure and to monitor the concentration of undesolved fibrous cellulose materials in suspension in a pulp-water mixture to determine what is generally known as the consistency of the pulp suspension. For example, the consistency of a pulp suspension is an important factor for the characteristics of the paper made from the suspension and has to be within rather narrow limits prior to applying it to the paper making machine.

The consistency of the pulp suspension is also an important factor in connection with measuring and monitoring the quality of the refining process as disclosed in our copending application Ser. No. 852,817 filed on Nov. 18, 1977 for "Apparatus and Method for Measuring the Degree of Refining of Pulp Fibers in the Preparation of Furnish for Paper Making". For use in measuring the quality of the refining process, it is necessary to utilize a known consistency which is much less than the consistency of the pulp suspension being refined, and which is usually of the order of 0.1% by weight. To assure reliable quality measurements, it is necessary that the consistency is measured and continuously monitored.

Since consistency is an important characteristic of the stock, many attempts have been made in the past to develop an on-line or flow technique to perform this measurement, but each of these has met with limited success. One prior art technique used to determine consistency is to measure the viscosity of the pulp suspension, but this approach is limited by uncontrolled variables, such as particle size and type, degree of pulp refining, degree of flocculation, surface conditions of the particles and concentration of inorganic additives.

Another prior art technique used to determine consistency has been the utilization of the optical transmission and reflection characteristics of the pulp suspension. However, this approach again was influenced by particle color, size and size distribution, the refractive index of particles, and by dissolved color. This technique is disclosed in U.S. Pat. No. 3,498,719 which issued on Mar. 3, 1970 to Wing et al for "Photoelectric Consistency Indicator for Pulp".

Another approach taken by the prior art to determine consistency is the utilization of the optical activity of the pulp suspension, and this approach has generally been much more successful than the other approaches. U.S. Pat. No. 3,518,003, which issued on June 30, 1970 to Meyn for "Procedure for Continuous Registration of the Concentration of Fiber Solutions" discloses the transmission of a plane polarized light beam through the pulp suspension and through a polarization analyzer having its transmission axis oriented in a selected direction with respect to the plane of polarization of the transmitted beam for reception by a photoelectric detector. The output signal from this photoelectric detector, and the signal from another photoelectric detector which receives the plane polarized light beam transmitted through the pulp suspension without transmission through the analyser, are processed to provide a signal which gives an indication of the pulp suspension consistency. However, this method, which relies only on one signal taking into account the optical activity of the pulp suspension and which largely ignores the effect of scattering in the suspension, has been found wanting in accuracy and repeatability and has been unsatisfactory from a calibration point of view.

It is therefore an object of the present invention to provide an apparatus and a method for determining the consistency of a pulp suspension which can easily and readily be calibrated to become independent of the transmission coefficient of the analyser and the characteristic of the detector providing the output signals.

It is a further object of the present invention to provide an apparatus and a method for determining the consistency of a pulp suspension which takes into account the imperfection of the polarizer and the analyzer, such as leakage, to provide accurate and repeatable measurements.

It is still a further object of the present invention to provide an apparatus and a method for determining the consistency of a pulp suspension which takes into account the reflection of light in a scattering medium.

SUMMARY OF THE INVENTION

In accordance with the present invention, there is provided a means and a method for determining the consistency of a pulp suspension by utilizing an in-line cell through which the pulp suspension is flowing and which has transmitted through the suspension a plane polarized beam of diffused light. The transmitted polarized light is received by at least two separate photoelectric detectors, after passing through overlying analyzers which, respectively, have their planes of transmission parallel and perpendicular to the plane of transmission of the transmitted beam of light. The output of the two photoelectric detectors, one providing a crossed signal commensurate with the light transmitted through crossed analyzers and the other providing a parallel signal commensurate with the light transmitted through parallel analyzers, is then processed to derive the ratio of (1) the difference of the crossed signal and the leakage component of the parallel signal and (2) the sum of the crossed and parallel signals, which ratio is proportional to the consistency of the pulp suspension.

BRIEF DESCRIPTION OF THE DRAWINGS

FIG. 1 is a diagrammatic, cross-sectional view of the pulp suspension consistency apparatus of the present invention;

FIG. 2 is an elevational view of a detector matrix for use with the apparatus of FIG. 1;

FIG. 3 is a graph showing the variations of the parallel signal and the crossed signal as a function of pulp consistency; and FIG. 4 is a graph showing the variations of the computed consistency with the measured consistency using oven dried weight.

DETAILED DESCRIPTION OF THE INVENTION

Referring now to FIG. 1 of the drawings, there is shown one embodiment of the consistency measuring apparatus 10 of the present invention. A pulp suspension 12 flows through a flow channel 14, which has a pair of opposed, transparent, parallel side walls (windows) 16 and 18, separated by a distance "W". The dimensions of flow channel 14, other than the side wall separation "W", are not important, which is the reason channel 14 is shown only diagrammatically. Generally speaking, flow channel 14 is dimensioned to provide the desired pulp suspension flow for purposes other than measuring or monitoring, and a section thereof is modified by replacing opposite walls with parallel transparent windows, such as 16 and 18, which may be either rectangular or circular. Windows 16 and 18 must be annealed, or otherwise treated, so that they are free of optical activity for reasons that will become better understood hereinafter.

A light source 20 is disposed on one side of channel or cell 14, and between source 20 and cell window 16 are placed, in the order stated, an infrared blocking filter 22, a collimating lens 24, a diffuser 26, and a polarizer 28. Blocking filter 22 is selected to have a transmission characteristic which blocks infrared waves to keep the heat from source 20 from reaching pulp suspension 12 and interfering with the measurement. Lens 22 converts the diverging light from source 20 into a parallel beam of light, and polarizer 28 polarizes this beam of light by transmitting only those components of the beam of light which has a plane of polarization in a selected direction. Diffuser 26 is provided to diffuse the light in the forward direction to decrease the dependence of the transmission on the presence of scattering particles in pulp suspension 12 and, in accordance with Kubelka-Munk laws that dependence can be minimized by providing an extended diffused source of light and an extended detector.

On the opposite side of cell 14 are disposed an analyzer 30, also referred to as the parallel analyzer because its plane of polarization is oriented so that it transmits polarized light having a plane of polarization parallel to the light beam from polarizer 28. Next to parallel analyzer 30 is an analyzer 32, also referred to as the perpendicular or crossed analyzer because its plane of polarization is oriented so that it transmits polarized light having a plane of polarization which is perpendicular to the light beam polarizer 28. Associated with analyzer 30, and receiving the light transmitted therethrough, is a photoelectric detector 34 which develops an output signal along lead 35 commensurate with the amount of parallel light transmitted through pulp suspension 12. Likewise, a photoelectric detector 36 is associated with crossed polarizer 32 which develops a signal on lead 37 which is commensurate with the amount of crossed light transmitted through pulp suspension 12. Both detectors are extended, i.e., have a large area to minimize dependence on scattering. The output of detectors 34 and 36 are applied to a processor 38 which, in turn, provides an output signal along lead 39 to an indicating meter 40, which may be directly calibrated in consistency units.

Referring now to FIG. 2 of the drawing, there is shown an arrangement or matrix 41 of analyzers which can be used instead of analyzers 30 and 32. More particularly, matrix 41 includes a parallel analyzer 42, crossed analyzer 43, a crossed analyzer 44 and a parallel analyzer 45, the terms parallel and crossed being relative to the plane of polarization of polarizer 38. Each analyzer is overlying a photoelectric detector which provides an output signal commensurate with the intensity of the light transmitted by the analyzer. Matrix 41, or any other type of matrix with a plurality of analyzers, provides for a more accurate and reliable measurement of the perpendicular and parallel signals because it receives transmitted light from different locations of cell 14 and can average out effects such as gravity, lack of fiber uniformity, or any other effect which may be sensitive to cell location in either a vertical or a horizontal direction.

The operation of this invention will now be explained with the help of FIG. 3 of the drawings which shows two curves 50 and 52 which, respectively, show the relation between the parallel light and the crossed light transmitted with change in consistency. More particularly, curve 50 shows the parallel output signals from detector 34 with increasing concentration and curve 52 shows the perpendicular output signal from detector 36 with increasing fiber concentration. For zero fiber concentration, when cell 14 is filled with pure water and assuming a perfect polarizer and analyzer, 100% of the parallel light will be transmitted and none of crossed light will be transmitted. As the concentration of fibers in the pulp suspension increases, the optical activity will rotate the plane of polarization and decrease the parallel transmitted light and increase the crossed transmitted light. Curves 50 and 52 also show the parallel and the crossed transmitted light approach one another which indicates a condition where the transmitted light is no longer polarized, which occurs at a concentration marked by point "A" in FIG. 3.

It is also to be understood that curves 50 and 52 are very sensitive to the important dimension "W" of the cell because the greater the wall separation, the greater is the amount of pulp suspension through which the polarized beam of light has to travel, and the greater is the optical activity. For the measurement to be meaningful, it is necessary that the parallel component and the perpendicular component be substantially different in amplitude and this will determine the range of consistency that can be measured by a given cell. For example, for a cell wall separation "W" equal to 0.25 inches, the measurable range is approximately 0 to 0.2% consistency, which corresponds to the point marked "B" in FIG. 4.

Referring once more to FIG. 3, there are also shown two lines 54 and 56 which represent, respectively, the total light transmitted through the pulp suspension with and without taking scattering and absorption into account. Line 54 shows that, without scattering and absorption, the total light transmitted through the pulp suspension is constant, in which case the parallel and crossed light transmitted, as shown by curves 50 and 52 would be symmetric with respect to the 50% line of intensity. However, there is scattering and absorption as the consistency increases, which accounts for the shape of curves 50 and 52, which when added to one another, would produce line 56 showing that the total amount of light transmitted is a function of the consistency of the pulp suspension.

It has been found that the consistency of fiber concentration is proportional to the perpendicular transmittance divided by the sum of the parallel transmittance and the perpendicular transmittance if the leakage of the polarizer-analyzer system for the crossed parallel light is ignored. The terms parallel and perpendicular have reference to the orientation of the plane of polarizer 28 and the formula is:

$$C = K \times \frac{I_{perp}}{I_{par} + I_{perp}} \quad (1)$$

where
C—computed consistency
K—system calibration constant
$I_{perp}$—measured transmittance of pulp suspension through crossed analyzer
$I_{par}$—measured transmittance of pulp suspension through parallel analyzer.

The relationship between the computed consistency given by equation (1) is plotted by curve 60 in FIG. 4 as a function of the measured consistency using the oven dried weight method. As can be seen from curve 60, the computed consistency is fairly linear with the measured consistency for low consistency values and then flattens out. Accordingly, the flatter the curve, the less meaningful the computed consistency. Processor 38 computes equation (1) and thereby provides an output signal which is a measure of consistency.

Using equation (1) to compute consistency also provides for very simple calibration of the system. The object is to make the output signal from detectors 34 and 36 equal for an equal amount of light reaching the detectors to eliminate the differences in the sensitivity of the individual detectors and in the transmissivity of the individual analyzers. This is done by removing polarizer 28 and adjusting the gains of the amplifiers, usually forming the output circuits of the detectors, for equal signal output. Because the processor computes a ratio, the channel calibration constants, being the same, simply cancel each other and the computed consistency is now independent of the analyzer transmissivity and the detector sensitivity.

It has been found that polarizers and analyzers are not perfect and that therefore equation (1) requires a correction term in the numerator. Computed consistency should be calculated in accordance with the following equation:

$$C = K \times \frac{I_{perp} - (K_2/K_1) I_{par}}{I_{perp} + I_{par}} \quad (2)$$

where
$K_1$—measured transmittance factor of parallel polarizer using pure water
$K_2$—measured transmittance factor of crossed polarizer using pure water (leakage constant).

It is to be understood that the second term in the numerator of equation (2) is of importance primarily for low fiber concentrations and that without this correction term, the error could be about 2% for a consistency of approximately 0.1%. It has been found from actual measurement that $K_1$ is about 0.7 and $K_2$ is about 0.0002 so that $K_2/K_1$ is about 0.00029.

This leakage correction is also important when diffused transmitted light is used, caused by diffuser 26, and when large area detectors are used to receive substantially all of the forward scattered and transmitted light.

When processor 38 is designated to compute the consistency, using equation (2), the calibration is likewise most convenient. The separate channels are equalized, as explained in connection with computing the consistency with the use of equation (1). Additionally, cell 14 is filled with pure water, and with the polarizer and the analyzers in place, a reading is taken of $I_{perp}$ and $I_{par}$ and $K_2/K_1$ is computed by taking the ratio of $I_{perp}$ and $I_{par}$ because the numerator of equation (2), for pure water, should be zero.

There has been described a method and an apparatus to compute the consistency of a pulp solution using the measured transmittance of the pulp solution through crossed and through parallel analyzers. Imperfections of the polarizer-analyzer systems are taken into account by utilizing a correction term in the numerator. Scattering errors are likewise minimized by utilizing an extended and diffused light source and extended detectors.

What is claimed is:
1. Consistency measuring apparatus for determining the concentration of fibers in a pulp suspension, said apparatus comprising:
   a cell containing a sample of the pulp suspension to be measured and having a pair of parallel, light transparent side walls;
   a plane polarized light source disposed on one side of said cell for developing and directing a polarized light beam through said transparent side walls of said cell for transmission through said sample;
   first and second plane polarized light analyzers disposed on the other side of said cell, adjacent to one another, and in the path of said transmitted light beam for directly intercepting said transmitted beam, said first analyzer having its plane of transmission parallel to and said second analyzer having its plane of transmission crossed with the plane of polarization of said light beam;
   first and second photoelectric detectors directly responsive to the light transmitted through said first and second analyzers, respectively, and developing first and second electrical signals representative of the transmitted light; and
   a signal processor responsive to said first and second signals and operative to develop a processed signal which is a measure of the consistency of said pulp suspension sample.
2. Consistency measuring apparatus in accordance with claim 1 which further includes a light diffuser for causing said polarized light beam to become diffused prior to transmission through said sample.
3. Consistency measuring apparatus in accordance with claim 1 in which said processed signal is proportional to the ratio of said second signal to the sum of said first and said second signals.
4. Consistency measuring apparatus in accordance with claim 1 in which said processed signal is proportional to:

$$\frac{S_2 - KS_1}{S_1 + S_2}$$

where $S_1$ is said first signal, $S_2$ is said second signal and K is a constant which is the ratio of the measured attenuation of crossed and parallel polarizers using pure water as said sample.
5. Consistency measuring apparatus in accordance with claim 2 in which said cell forms a portion of a flow channel through which the pulp suspension flows for an in-line measurement of the consistency.
6. Consistency measuring apparatus in accordance with claim 2 further including a filter for blocking the infrared radiation from said light source, said filter being disposed between said source and said cell.

7. Consistency measuring apparatus in accordance with claim 1 in which said plane polarized light source includes a point source of light; a blocking filter in the path of the light from said source to eliminate transmission of infrared radiation; a lens for collimating the light from said source; a light diffuser for diffusing the light; and a plane polarizer to pass only light polarized in a selected direction.

8. Consistency measuring apparatus in accordance with claim 4 including an indicator which is responsive to said processed signal and operative to provide a visual indication of the consistency of the pulp suspension.

9. A method for determining the consistency of a pulp suspension comprising the steps of:
   transmitting a beam of plane polarized light through a sample of pulp suspension having its fibers uniformly distributed therethrough;
   passing the transmitted polarized light directly through an analyzer whose plane of transmission is parallel to the plane of the polarized light and developing a first electrical signal which is directly proportional to the amount of parallel transmitted light;
   passing the transmitted polarized light directly through an analyzer whose plane of transmission is crossed with the plane of transmission of the polarized light and developing a second electrical signal which is directly proportional to the amount of crossed transmitted light; and
   processing said first and second signals to derive a processed signal which is commensurate with the consistency of the pulp suspension sample.

10. A method for determining the consistency of a pulp suspension in accordance with claim 9 in which the light is diffused before it is transmitted through the sample.

11. A method for determining the consistency of a pulp suspension in accordance with claim 10 in which the first and second signals are processed in accordance with the formula:

$$\frac{S_2 - KS_1}{S_1 + S_2}$$

in which $S_1$ is said first signal, $S_2$ is said second signal and K is a constant which is the ratio of the measured attenuation of crossed and parallel polarizers using pure water as said sample.

* * * * *